(12) United States Patent
Messenger et al.

(10) Patent No.: US 7,763,473 B2
(45) Date of Patent: Jul. 27, 2010

(54) SAMPLE APPLICATORS FOR ANALYTICAL ASSAYS

(75) Inventors: Lowry Jonathan Messenger, Escondido, CA (US); Simon Charles Khoury, Del Mar, CA (US)

(73) Assignee: Scripps Laboratories, Inc., San Diego, CA (US)

( * ) Notice: Subject to any disclaimer, the term of this patent is extended or adjusted under 35 U.S.C. 154(b) by 127 days.

(21) Appl. No.: 11/490,874

(22) Filed: Jul. 21, 2006

(65) Prior Publication Data

US 2008/0026453 A1 Jan. 31, 2008

(51) Int. Cl.
- *B01L 3/02* (2006.01)
- *B01L 9/00* (2006.01)
- *C12Q 1/00* (2006.01)
- *G01N 1/10* (2006.01)
- *G01N 33/53* (2006.01)

(52) U.S. Cl. .................. 436/180; 422/100; 422/104; 435/4; 436/807

(58) Field of Classification Search .................. 422/100, 422/104; 435/4; 436/180, 807
See application file for complete search history.

(56) References Cited

U.S. PATENT DOCUMENTS

| | | | |
|---|---|---|---|
| 4,006,750 A | 2/1977 | Chodorow | |
| 4,334,879 A | 6/1982 | Fujimori | |
| 5,405,516 A | 4/1995 | Bellon | |
| 5,538,023 A | 7/1996 | Oczkowski et al. | |
| D410,115 S | 5/1999 | Chodorow | |
| 6,036,659 A | 3/2000 | Ray et al. | |
| 6,085,760 A | 7/2000 | Chodorow | |
| 6,177,283 B1 | 1/2001 | Ray | |
| 6,235,539 B1 | 5/2001 | Carpenter | |
| 6,258,045 B1 | 7/2001 | Ray | |
| 6,265,223 B1 | 7/2001 | Ray | |
| 6,309,887 B1 | 10/2001 | Ray | |
| 6,544,395 B1 | 4/2003 | Merchant et al. | |
| 6,544,457 B1 | 4/2003 | Rieser | |
| 6,555,390 B2 | 4/2003 | Chandler | |
| D489,490 S | 5/2004 | Chodorow | |
| 6,766,808 B2 | 7/2004 | Gwen | |
| 6,841,159 B2 | 1/2005 | Simonson | |
| 7,478,958 B2 * | 1/2009 | Ramet | 401/124 |
| 2006/0148096 A1 * | 7/2006 | Jina | 436/514 |
| 2007/0141564 A1 * | 6/2007 | Aberl et al. | 435/5 |
| 2008/0031779 A1 * | 2/2008 | Polito et al. | 422/68.1 |

FOREIGN PATENT DOCUMENTS

| | | |
|---|---|---|
| WO | WO 02/28310 | 4/2002 |
| WO | WO 2004/084760 | 10/2004 |
| WO | WO 2005/092237 | 10/2005 |

* cited by examiner

*Primary Examiner*—Gailene R Gabel
*Assistant Examiner*—Jacqueline Diramio
(74) *Attorney, Agent, or Firm*—Knobbe, Martens, Olson & Bear LLP

(57) ABSTRACT

A liquid applicator for applying a liquid sample to a liquid receiving surface is disclosed. The liquid applicator comprises a bibulous line to hold a first predetermined volume of liquid for application to a liquid receiving surface. A second predetermined volume less than or equal to the first predetermined volume is applied to the liquid receiving surface in a substantially uniform and consistent pattern. Systems and methods for using embodiments of the liquid applicators are also disclosed.

13 Claims, 2 Drawing Sheets

SAMPLE APPLICATORS FOR ANALYTICAL ASSAYS

BACKGROUND

1. Field of the Invention

This invention relates to sample applicators for analytical assays.

2. Description of the Related Art

Various types of sample applicators for analytical assays have been disclosed. Sample applicators specifically for blood sample assays are also known in the art. See, for example, U.S. Pat. Nos. 6,036,659; 6,177,283; 6,258,045; 6,265,223; and 6,309,887. Applying a uniform volume and/or shape of a sample to an assay device can be important to optimize performance of the assay. Previous systems attempt, through various methods, to apply a predetermined volume of liquid in a uniform distribution to an assay. For example, U.S. Pat. No. 4,334,879 discloses an applicator blade capable of absorbing sample and being pressed onto an applicator film. U.S. Pat. No. 5,405,516 discloses an applicator with a planar projecting element and a stiffening element that employs a hydrophobic mixture on the applicator to avoid sample leaching or blotting of an assay. U.S. Pat. No. 6,544,395 discloses an applicator blade with an applicator tip and a barrier that limits an amount of liquid the sample applicator may retain. Such systems and methods may also require separation of liquid sample (by the sample applicator) or other treatment of the sample or of the sample applicator prior to the administration of the sample to the assay.

SUMMARY

In one embodiment a method for applying a liquid to a liquid receiving surface is provided. The method comprises providing a bibulous line adapted to receive a first volume of a liquid, applying to the line a liquid volume less than or equal to the first volume, contacting the line with a liquid-receiving surface and transferring from the line to the liquid-receiving surface at least a portion of the first volume.

In some embodiments the bibulous line is under tension. In some embodiments the bibulous line is held by a frame. In some embodiments the liquid-receiving surface is a portion of an assay. In some embodiments the assay is a lateral flow assay. In some embodiments the method further comprises taking a first measurement of the liquid on the liquid receiving surface. In some embodiments the method further comprises taking a second measurement of the liquid on the liquid receiving surface. In some embodiments the first measurement and the second measurement are taken at an application site of the liquid receiving surface. In some embodiments a portion of the first volume in the line comprises at least one reagent. In some embodiments the method further comprises allowing at least the portion of the first volume to dry on the bibulous line. In some embodiments the first volume is a predetermined volume.

In another embodiment an assay device comprises an assay component, comprising a guide formed on a sample receiving surface and a bibulous line held on a frame. The bibulous line comprises at least one of a reagent and a sample stabilizer. The frame is configured to mate with the guide.

In some embodiments the bibulous line is at least one of thread, yarn, strand, fiber, cord and string. In some embodiments the bibulous line comprises one filament. In some embodiments the bibulous line comprises multiple filaments.

In another embodiment a system for applying a sample to an assay comprises a sample receiving surface, wherein the sample receiving surface is adapted for a liquid to flow therethough and a sample applicator, wherein the sample applicator comprises a bibulous line stretched to form a substantially straight line and wherein the substantially straight line is configured to deposit a predetermined amount of sample in a substantially linear pattern on the sample receiving surface.

In another embodiment a method of manufacturing a sample applicator comprises providing a sample applicator comprising a bibulous line extended on a frame, wherein a portion of the bibulous line is stretched to form a substantially straight edge, applying an assay reagent or sample treatment reagent to the bibulous line and drying the reagent on the bibulous line.

In some embodiments the bibulous line is adapted to hold a predetermined volume of liquid. In some embodiments the bibulous line is configured to transfer a volume less than or equal to the predetermined volume to an assay surface.

In another embodiment a kit comprises a sample receiving surface in or on an assay device and an applicator comprising a bibulous line held on a frame. In some embodiments a portion of the bibulous line is under tension. In some embodiments the frame is configured to mate with a guide on the assay device.

In another embodiment a method of collecting a biological sample comprises providing a line of bibulous material held on a frame and applying a biological sample to be analyzed to the line of bibulous material.

In some embodiments the method further comprises drying the biological sample on the line in a first geographical location, transporting the dried biological sample to a second geographical location remote from the first location and then analyzing the biological sample. In some embodiments the method further comprises storing the line containing the biological sample, wherein the line further comprises at least one sample-stabilizing reagent.

DETAILED DESCRIPTION OF THE PREFERRED EMBODIMENT

Figure 1:
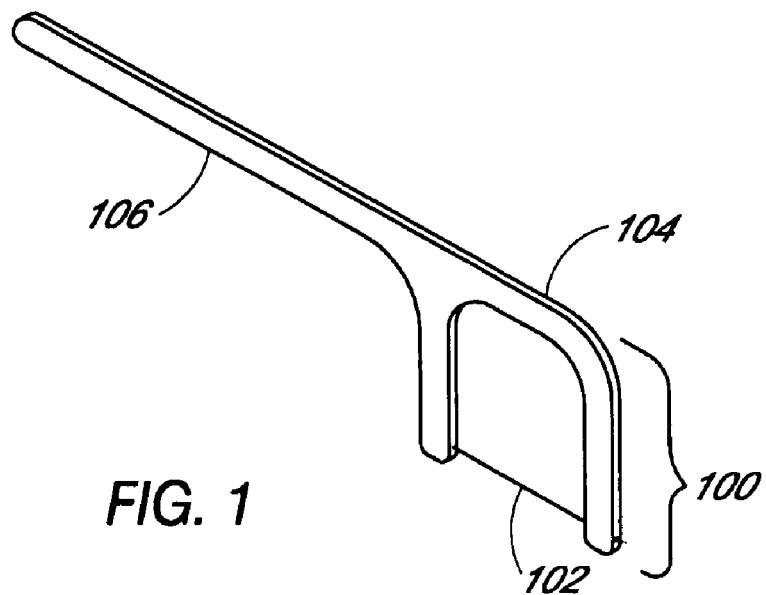
FIG. 1 shows one embodiment of a liquid applicator.

Many assay devices that are configured to receive a sample require a relatively controlled or prescribed placement of the sample in or on the assay device. For example, in many lateral flow assays, a sample (usually a liquid sample) is placed on a sample receiving surface, after which the sample is analyzed in the device. Typically, samples are initially deposited on a sample-receiving area of a lateral flow assay. Wash liquid (or other liquid) flow then mobilize sample and/or move at least some component of the sample to a predetermined second location different than the sample-receiving area. Flow-through assays involve depositing a sample in or on a surface or membrane, after which liquid mobilizes a portion of the sample to move it from the sample-receiving area.

In lateral flow assays, flow-through assays and other types of assays, sample application can be a critical step. Often, it is desirable to deliver a predetermined volume of sample to the assay device. Sometimes, it is desirable to deliver the sample uniformly to a predetermined area in a predetermined pattern. If too much sample is delivered to the assay, the sample volume overwhelms or masks the ability of assay reagents to capture and measure or display an analyte. This, in turn, may interfere with the accuracy of the assay.

One way to address the problem of either inadequate or excess sample is to use a sample applicator that administers a predetermined volume (or predetermined volume range) of sample. Potential structures that could quantitatively or semi-quantitatively deliver a desired volume might include various types of droppers or syringes. These sample applicators may consistently administer a relatively uniform volume, but do not guarantee uniform distribution of the sample to the assay. For example, a circular drop of liquid sample placed on a lateral flow assay does not migrate equally; because the buffer flows faster in the areas of least resistance, most of the buffer flows around the circular drop and less sample flows from the middle of the sample.

Thus, a method and a system are disclosed for providing a substantially uniform distribution of a predetermined volume (or volume range) of liquid to a sample receiving surface. In some embodiments the method and the system use a bibulous line adapted to receive a first volume of a liquid. After the bibulous line has received a liquid volume less than or equal to the first volume, the bibulous line is brought into contact with a liquid-receiving surface, such that the bibulous line transfers some or all of the liquid volume to the liquid-receiving surface.

In some embodiments the bibulous line comprises at least one of a thread, yarn, strand, fiber, cord, or string. In some embodiments the bibulous line is a single filament. In some embodiments the bibulous line is woven, braided or spun from individual fibers, strings, or threads. In some embodiments the bibulous line is nonwoven, unbraided and/or unspun. In some embodiments the bibulous line comprises a plurality of generally parallel fibers or strands. (It is acknowledged that in certain contexts in the art, fibers are considered to have relative short length when compared to filaments. Herein, however, these terms are employed interchangeably.) In some embodiments the bibulous line comprises other materials consistent with the function of the bibulous line. In some embodiments the bibulous line includes combinations of the above materials. In some embodiments the bibulous line is configured to wick up or otherwise contain a volume or volume range of a liquid, typically a sample. In some embodiments a liquid volume comprises one or more reagents or other assay materials. In some embodiments the sample-receiving portion of the bibulous line comprises a predetermined specific length so that a predetermined volume of liquid media is held by the bibulous line.

FIG. 1 illustrates one embodiment of a liquid applicator 100. In this embodiment, the liquid applicator 100 comprises a bibulous line 102 stretched upon a frame 104. The bibulous line 102 is attached to a frame 104 and stretched so as to be under tension. In some embodiments a frame 104 is composed or formed of a synthetic polymer, such as a thermoplastic or thermoset material, or of wood, metal, fiber, composite, or any other suitable structural material. In the illustrated embodiment, an optional handle 106 is attached to the frame 104. The handle 106 allows for ease of manipulation of the bibulous line 102 when applying sample thereto or when applying the line 102 to a liquid receiving surface.

As discussed herein, some embodiments of the invention include constructing the liquid applicator 100 to include a specific thickness and length of the bibulous line 102 so as to control the volume of the liquid absorbed by the bibulous line 102. Thus, in some embodiments, a bibulous line of specified diameter and length holds only a predetermined volume of a liquid. Thus, the predetermined volume (within relatively narrow constraints, such as plus or minus 20%) is taken up by the bibulous line when the bibulous line is contacted with an excess of sample. In this manner, volumes substantially exceeding the predetermined volume are never delivered to the assay. This is in sharp contrast to the direct application of, for example, a drop of blood to the assay, where the volume of the drop varies by 25%, 50%, 100%, or more. In a preferred embodiment, the bibulous line 102 comprises at least one fiber and advantageously wicks up liquid sample along substantially the entire length of the bibulous line 102 before it is brought into contact with a sample-receiving area of an assay device.

In some embodiments the bibulous line 102 is used to hold a variety of liquid media prior to contacting a liquid receiving surface. For example, in some embodiments a portion of the liquid volume includes at least one reagent. The bibulous line 102 is preloaded with calibrator or control material for calibration and quality control of analytical assays. Similarly, in some embodiments the bibulous line 102 is impregnated with a buffer, a lysing agent, an anticoagulant, another reagent or assay component, or some combination thereof, in liquid or solid form. In some embodiments a liquid is allowed to dry on the bibulous line 102.

In some embodiments, the liquid applicator 100 is useful for remotely collection blood for assay at a central location. In some preferred embodiments the liquid applicator 100 is particularly useful for collection of small biological samples such as acquiring fingerstick blood directly from a finger and subsequently applying that sample uniformly to a liquid receiving surface such as an assay strip for measuring glycated hemoglobin.

Figure 2:
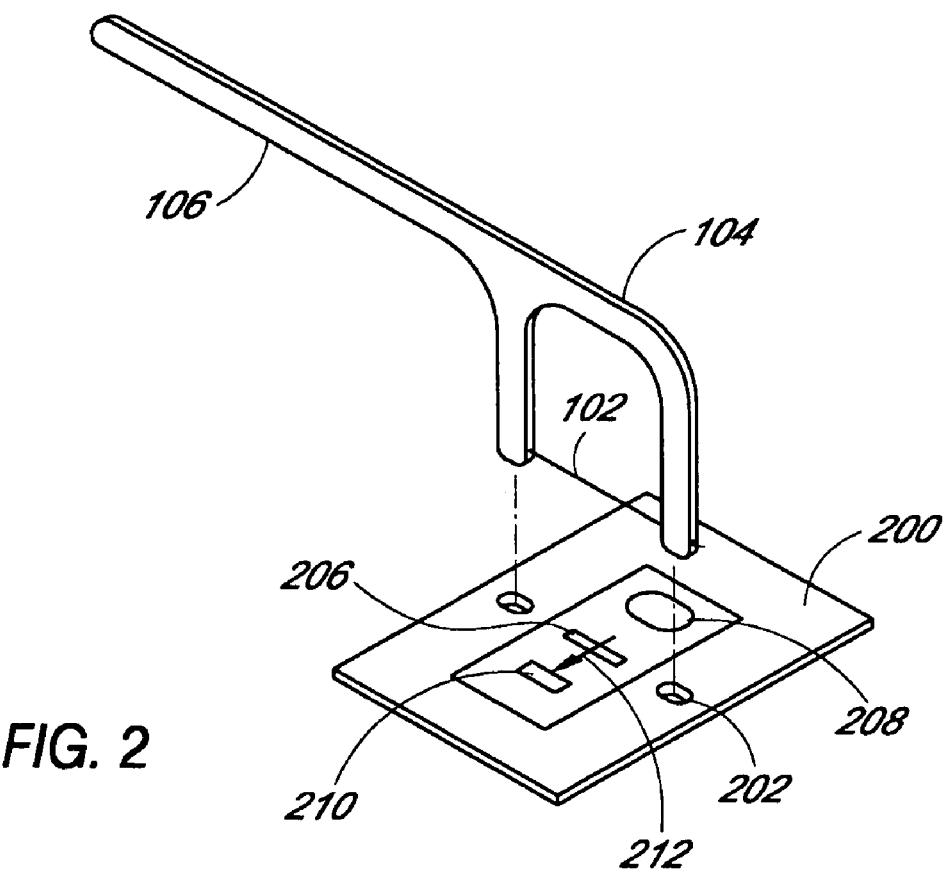
FIG. 2 shows a liquid applicator interacting with a liquid-receiving surface on an assay.

FIG. 2 illustrates another embodiment with a liquid applicator 100 comprising a bibulous line 102 stretched upon a frame 104. FIG. 2 also illustrates an embodiment of an assay device 200 with guides 202 for aligning the liquid applicator 100 with the assay device 200. In other embodiments a single guide 202 aligns the liquid applicator 100 with the assay device 200. In some preferred embodiments the guides 202 comprise guide holes, or any other suitable mating structure for effecting registration between the liquid applicator 100 and the assay device 200. When the liquid applicator 100 is properly aligned or registered with the guides 202, the bibulous line 102 on the liquid applicator 100 contacts the assay device 200. The depth of the guide holes 202 and the distance of the bibulous line 102 from the base of the frame control the amount of pressure that the bibulous line 102 applies to the sample assay 200, thus controlling the volume of sample transferred to the assay.

Further, the guide holes 202 provide a precise and accurate application of sample to the assay 200. A combination of tension of the bibulous line 102 and the depth of the guide holes 202 on the assay 200 ensures control of the pattern and the force of contact between the bibulous line 102 and the liquid receiving surface 206. Thus, the guide holes 202 control the pattern and the volume of liquid transfer from the liquid applicator 100. In certain embodiments the liquid applicator 100 snaps loosely into place in the guide holes 202 to signal that the liquid applicator 100 has been inserted properly.

In some embodiments, when the liquid applicator 100 contacts the sample assay 200, the bibulous line 102 contacts a liquid receiving surface 206 on the assay device 200. When a volume of liquid is held by the bibulous line 102, the bibulous line 102 is then contacted with the liquid receiving surface 206 so that a portion of the liquid volume in the bibulous line 102 is transferred to the liquid receiving surface 206 in a predictable amount. Upon contact with the liquid receiving surface 206, the bibulous line 102 dispenses some or all of the liquid volume held by it in a uniform linear pattern on the liquid receiving surface 206. In some embodiments, the assay device 200 is a lateral flow assay. In some embodiments assay measurements are taken at a single site (for example, the sample receiving surface 206). In other embodiments assay measurements are taken at one or more locations remote from the sample receiving surface 206. For example, in some embodiments measurements are taken "downstream" from the sample receiving surface 206. In some embodiments the bibulous line 102 is used to apply samples to various surfaces including gels, papers and membranes used in other types of assays, including chromatography, electrophoresis, and isoelectric focusing. In some embodiments the bibulous line 102 is used to apply samples to media such as silica gel for use in thin layer chromatography or nitrocellulose for use in an immunoassay.

Finally, FIG. 2 also illustrates a liquid flow in a lateral flow assay from a first area 208 toward a second area 210. The direction of flow is indicated by the arrow 212. In this embodiment, excess or unbound analyte and/or sample is washed off the second area 210.

In practice there are many advantages to the methods and system discussed herein. One such advantage is easy sampling directly from a fingerstick blood sample. For example, in some embodiments the liquid applicator 100 does not obscure the vision of a person who is obtaining the sample from the fingerstick. Thus, sample collection is accomplished simply by contacting the bibulous line 102 with the blood obtained from the finger. Moreover, collection of a desired sample volume is self-limiting because collection stops when the bibulous line 102 is saturated with blood. Thus, it is easy for the operator to know when an adequate sample volume has been collected. In some embodiments the bibulous line 102 contacts the blood on a fingerstick without contaminating the frame 104 of the liquid applicator 100; the spread of the frame 104 is such that combined with the curvature of a finger, only the bibulous line 102 contacts the blood and/or the finger subjected to the fingerstick.

In preferred embodiments, another advantage of the liquid applicator 100 is that the volume of liquid is relatively precise and is applied in a uniform (e.g. substantially -straight) line across the liquid receiving surface 206, transverse to the direction of liquid flow in the assay. Thus, the applied volume migrates uniformly through the relevant portions of the assay device 200. In some embodiments the liquid applicator 100 is designed to fit into the assay device or into a meter holding the assay device. The design of the liquid applicator 100 ensures proper orientation of the liquid applicator 100 as it is placed into guide holes 202. For instance, a peg-shaped foot being funneled into a cylinder ensures that the bibulous line 102 is substantially level and aligned both side-to-side and front-to-back, as it makes contact with the assay device.

Figure 3:
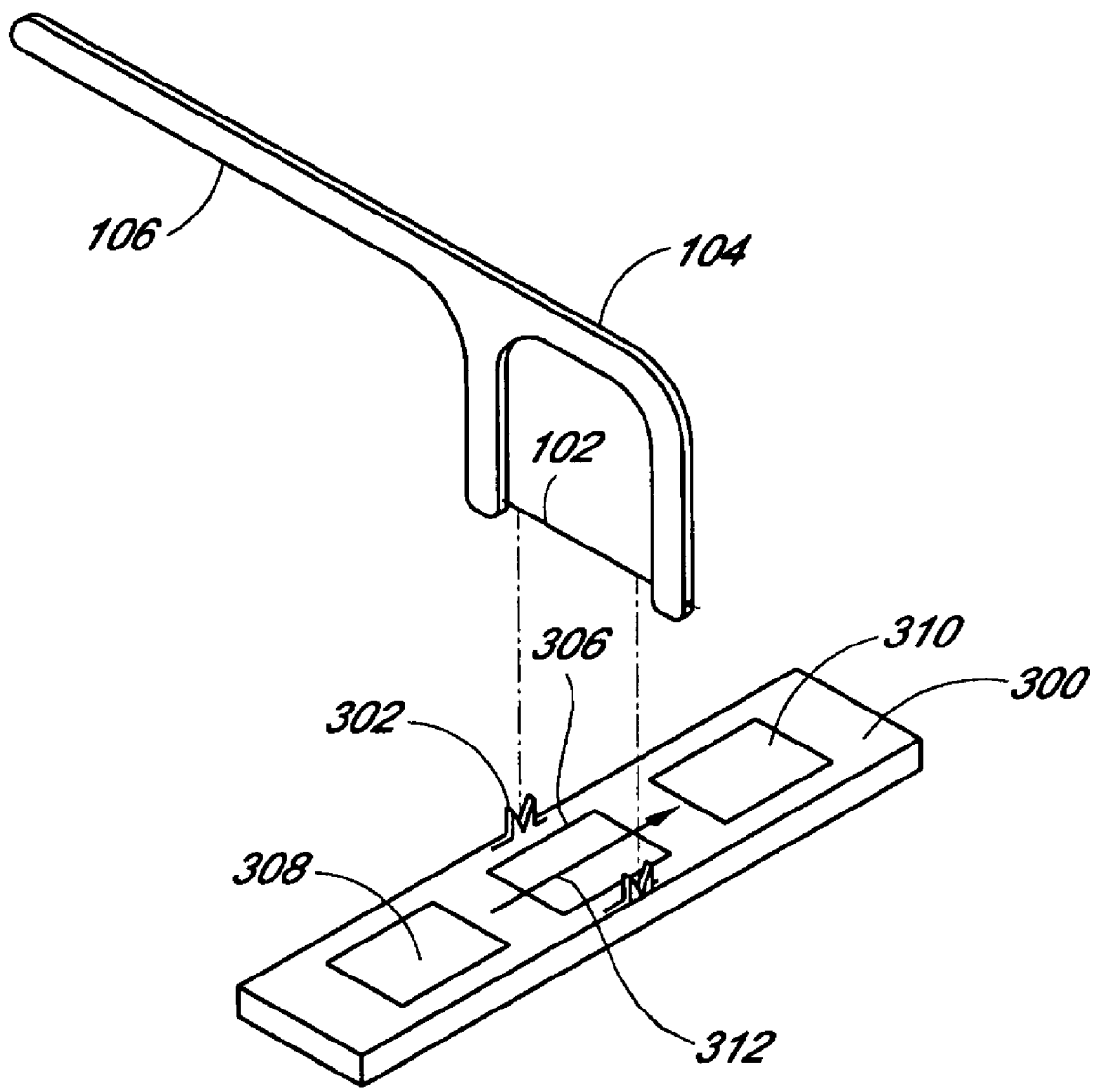
FIG. 3 shows another embodiment of a liquid receiving surface on an assay.

FIG. 3 shows a perspective view of another embodiment of an assay device 300. Cleft posts 302 interact with a bibulous line 102 so as to allow the bibulous line 102 to contact a liquid receiving area 306. In some embodiments a single cleft post 302 may be used to interact with a bibulous line 102 and thereby guide the bibulous line 102 to contact the liquid receiving area 306. When the bibulous line 102 is placed in the antipex of the cleft posts 302, the bibulous line 102 is aligned so as to transfer a predetermined volume of liquid in a substantially linear pattern on the liquid receiving area 306. Similar to the embodiment of FIG. 2, flowing liquid moves from a first location 308 to a second location 310 in a direction of migration 312.

In some embodiments, the liquid applicator 100 is used to produce a unitized control ideal for use in unitized assays in decentralized locations. Control material is pre-applied to the bibulous line and dried. In some embodiments liquid applicators 100 are packaged individually. The volume of control applied is sufficient to run the assay, but not excessive, thereby ensuring low cost. The stability of a dried control is advantageous, especially if the control is individually packaged with desiccant. In some embodiments control is dried on the bibulous line 102 with stabilizers. In some embodiments a buffer used to run the assay is used to reconstitute the control material. In some embodiments the reconstitution buffer is supplied separately. In some embodiments levels of control are applied to the bibulous line 102 in varying amounts.

In preferred embodiments a dry control is soluble and dissolves with a minimal volume of buffer. In the case of hemoglobin A1c, a lysate of washed red blood cells is soluble after it is applied to the bibulous line 102 of the liquid applicator 100 and dried. The lysate contains a non-ionic detergent, which dissolves easily and transfers to the liquid receiving surface 206 when eluted with at least one drop of buffer applied to the assay. In some embodiments the buffer is added directly to the bibulous line 102 to solubilize the dried hemoglobin. In other embodiments, the buffer solubilizes the dried hemoglobin when the bibulous line 102 contacts the assay. In some embodiments the buffer used to run the assay contains detergent. If problems with dissolution still occur, different additives are used. In some embodiments, the bibulous line 102 is lyophilized after the control material is applied. If problems occur because of oxidation of the hemoglobin on the bibulous line 102, the liquid applicator 100 is sealed in an inert gas atmosphere.

In some embodiments a calibrator solution of a proper concentration is applied to a liquid applicator 100 at the point of use of the assay as described with respect to various embodiments discussed herein. The calibrator solution is used in the same manner and is able to interface with the meter to provide calibration.

In some embodiments, a liquid applicator 100 is used as a remote sampling device to collect biological samples such as blood or other bodily fluids. The sample is then dried on the bibulous line 102 and the liquid applicator 100 is assayed at a different location from the sampling. The liquid applicator 100 is then used in the same manner as the applicators bathed with quality control material. In one embodiment, the liquid applicator 100 is placed into guides on a meter and the dried sample on the bibulous line 102 is eluted with a buffer onto the assay device. In some embodiments the bibulous line 102 is treated with buffer-containing detergent and anticoagulant (in the case of blood being sampled) in order for the sample to elute properly from the bibulous line 102.

It will be appreciated by those skilled in the art that various modifications and changes may be made without departing from the scope of the invention. Such modifications and changes are intended to fall within the scope of the invention, as defined by the appended claims.

What is claimed is:

1. A method of applying a liquid to a liquid-receiving surface, the method comprising:
   providing a bibulous material that is stretched into a tensioned line, the line adapted to receive a first volume of a liquid;
   applying to said line a liquid volume less than or equal to said first volume;
   contacting said line with a liquid-receiving surface, wherein said liquid-receiving surface is a portion of an assay; and
   transferring from said line to said liquid-receiving surface at least a portion of said first volume.

2. The method of claim 1, wherein said bibulous material is held by a frame.

3. The method of claim 1, wherein said assay is a lateral flow assay.

4. The method of claim 3 further comprising taking a first measurement of said liquid on said liquid receiving surface.

5. The method of claim 4 further comprising taking a second measurement of said liquid on said liquid receiving surface.

6. The method of claim 5, wherein said first measurement and said second measurement are taken at an application site of said liquid receiving surface.

7. The method of claim 1, wherein a portion of said first volume in said line comprises at least one reagent.

8. The method of claim 7 further comprising allowing at least said portion of said first volume to dry on said bibulous material.

9. The method of claim 1, wherein said first volume is a predetermined volume.

10. The method of claim 1, wherein a portion of said first volume in said line comprises blood.

11. The method of claim 10, wherein said blood comprises whole blood.

12. The method of claim 10 further comprising allowing at least said portion of said first volume to dry on said bibulous material.

13. The method of claim 7, wherein said at least one reagent comprises a liquid stabilizing reagent.

* * * * *